United States Patent [19]
Miyagi et al.

[11] Patent Number: 5,496,338
[45] Date of Patent: Mar. 5, 1996

[54] MEDICAL INSTRUMENT FOR TREATING SINUSITIS

[75] Inventors: Kunihiko Miyagi; Hidetoshi Yoshizawa, both of Tokyo,, Japan

[73] Assignee: Machida Endoscope Co., Ltd., Tokyo, Japan

[21] Appl. No.: 260,828

[22] Filed: Jun. 16, 1994

[30] Foreign Application Priority Data

Jun. 29, 1993 [JP] Japan ................................ 5-184382

[51] Int. Cl.⁶ ............................ A61F 9/00; A61F 11/00; A46B 13/00
[52] U.S. Cl. ................................ 606/162; 15/23
[58] Field of Search ................... 606/162, 159, 606/80, 84–85; 15/23; 604/95; 128/756

[56] References Cited

U.S. PATENT DOCUMENTS

| | | | |
|---|---|---|---|
| 374,026 | 11/1887 | Williams | 606/162 X |
| 1,272,170 | 7/1918 | Ziegler | 606/162 X |
| 1,520,908 | 12/1924 | Meyer | 606/162 |
| 3,859,684 | 1/1975 | Moskwinski | 15/23 |
| 4,603,448 | 8/1986 | Middleton et al. | 15/23 X |
| 5,406,669 | 4/1995 | Lesiw | 15/23 X |

FOREIGN PATENT DOCUMENTS 421999  1/1935  United Kingdom ............... 128/261

*Primary Examiner*—Stephen C. Pellegrino
*Assistant Examiner*—Nancy Mulcare
*Attorney, Agent, or Firm*—Fish & Richardson

[57] ABSTRACT

A medical instrument for treating sinusitis has a body, an insert tube extending from a distal end of the body, and an angle portion extending from a distal end of the insert tube. The angle portion is bent by a remote control member mounted on the body, through a wire. A motor is mounted on the body. The medical instrument also has a brush. This brush has an elongated rotation transmission portion extending through the insert tube and the angle tube, and a brush portion attached to a distal end of the rotation transmission portion. A basal portion of the rotation transmission portion is connected to the motor. The brush portion is allowed to protect from a distal end of the angle tube. At least that portion of the rotation transmission portion extending through the angle tube is bendable. Therefore, when the motor is rotated in the state that the angle portion is bent, the brush portion is rotated.

6 Claims, 6 Drawing Sheets

MEDICAL INSTRUMENT FOR TREATING SINUSITIS

BACKGROUND OF THE INVENTION

This invention relates to a medical instrument for treating inflammation of the paranasal sinus, i.e., sinusitis.

Sinusitis, for example, maxillary sinusitis, is a disease in which a mucous membrane on an inner surface of the maxillary sinus is inflamed or peeled and finally suppurated to produce pus. As one method for treating the maxillary sinus, there is known a method, in which the peeled mucous membrane is removed by an elongated spatula and drawn or sucked by a drawing instrument or suction apparatus.

In the case where the spatula is used, however, it is difficult to insert the spatula deep into the curved maxillary sinus and therefore, some of the peeled mucous membrane are often left unremoved. Also, repetition of a reciprocal motion of the spatula cannot assuredly remove the mucous membrane which is peeled off over the entire inner periphery of the maxillary sinus. Thus, the effect of treatment using the spatula is not entirely satisfactory.

SUMMARY OF THE INVENTION

It is therefore an object of the present invention to provide a medical instrument which is capable of remarkably improving the effect of treatment of sinusitis.

According to the present invention, there is provided a medical instrument for treating sinusitis, comprising:

(a) a body;

(b) an insert tube extending from the body;

(c) an angle tube extending from a distal end of the insert tube;

(d) a remote control member mounted on the body and adapted to remote control the angle tube through a control wire extending through the insert tube and the angle tube;

(e) a motor mounted on the body; and (d) a brush having an elongated rotation transmission portion whose rear end is connected to the motor, and a brush portion attached to a distal end of the rotation transmission portion, the rotation transmission portion being allowed to extend through the insert tube and the angle tube, at least that portion of the rotation transmission portion corresponding to the angle tube being bendable, the brush portion being allowed to project outside from a distal end of the angle tube.

DETAILED DESCRIPTION OF THE EMBODIMENT

Figure 1:
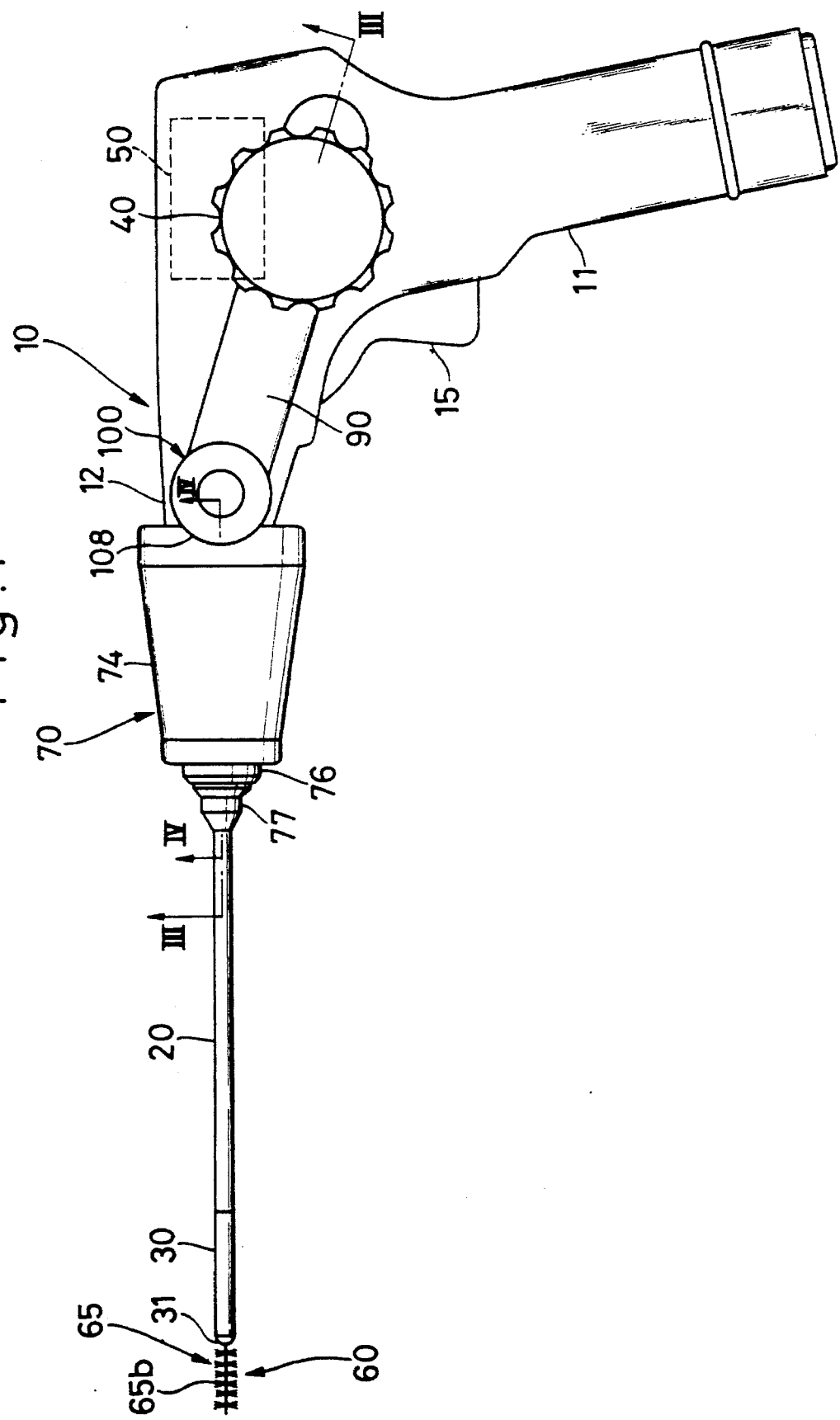
FIG. 1 is a side view of a medical instrument for treating sinusitis according to one embodiment of the present invention.

The present invention will be described in detail with reference to the accompanying drawings. FIG. 1 shows a medical instrument used for treating sinusitis. This will be briefly described. The medical instrument comprises a hollow body 10, a hard insert tube 20 extending from the body 10, and an angle tube 30 extending from a distal end of the insert tube 20. The angle tube 30 is bent by a control dial 40 (remote control member) mounted on the body 10. The body 10 contains a motor 50. The medical instrument further comprises a brush 60. A rear end of the brush 60 is removably connected to the motor 50 so that the brush 60 is rotated by the motor 50. The brush 60 is allowed to extend through the insert tube 20 and the angle tube 30. A distal end of the brush 60 is allowed to project from a distal end of the angle tube 30.

Next, the construction of each component part will be described in detail. As shown in FIG. 1, the body 10 has a hollow Gun-like configuration. The body 10 includes a grip portion 11, and an extension portion extending from an upper end of the Grip portion 11 in a direction intersecting the grip portion 11 (in other words, the extension portion extending forwardly).

Figure 3:
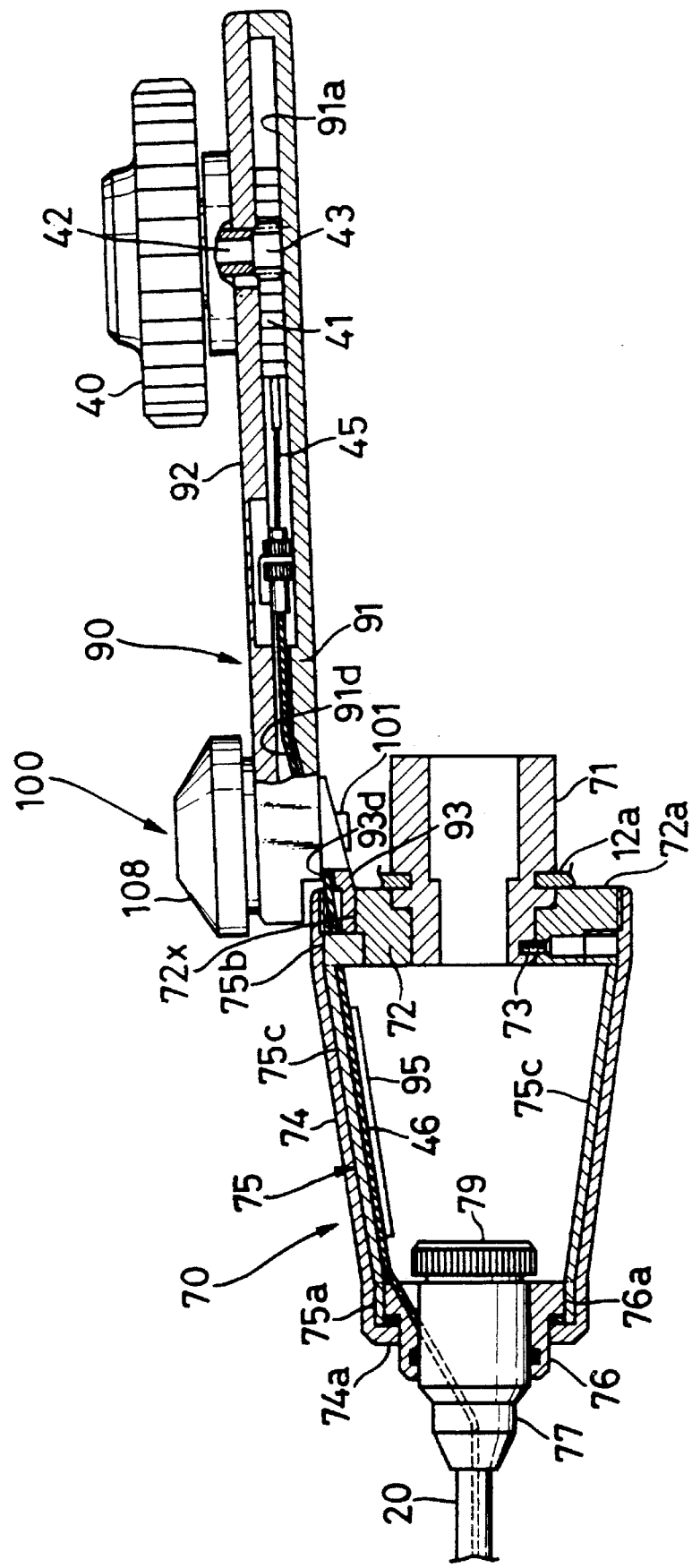
FIG. 3 is an enlarged sectional view of an important portion of the medical instrument taken on line III—III of FIG. 1.
Figure 4:
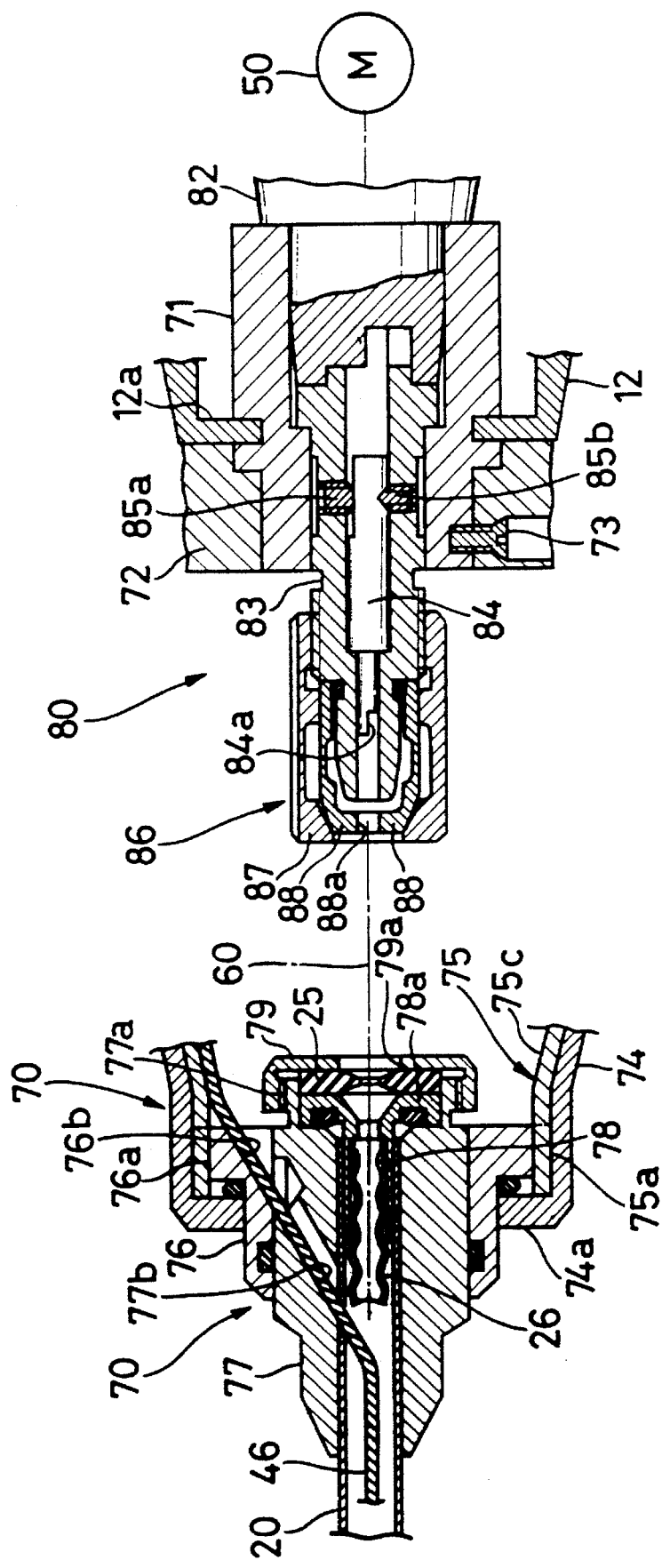
FIG. 4 is likewise an enlarged sectional view of an important portion taken on line IV—IV of FIG. 1, showing a connecting mechanism for connecting a brush and an insert tube to a body.

As best shown in FIGS. 3 and 4, the insert tube 20 is connected to a distal end of the extension portion 12 of the body 10 through a generally cylindrical connecting mechanism 70. This connecting mechanism 70 has a sleeve 71. This sleeve 71 is allowed to extend through a distal end wall 12a of the extension portion 12 and fixed to the distal end wall 12a. A ring 72 is fitted to an outer periphery of the sleeve 71 and fixed by a screw 73. The ring 72 is provided on a rear end outer periphery thereof with a flange 72a projecting radially outwardly. A rear end portion of a tapered sleeve 74 is threadedly engaged with an outer periphery of the flange 72a. A support 75 is received in the sleeve 74. This support 75 includes a front ring portion 75a, a rear ring portion 75b, and a pair of elongated connecting portions 75c for connecting the front and rear ring portions 75a and 75b. When the sleeve 74 is threadedly engaged with the ring 72, the ring portion 75a is brought into abutment with a flange 74 formed on a distal end of the sleeve 74 and the ring portion 75b is brought into abutment with the flange 72a of the ring 72, thereby fixing the support 75 within the sleeve 12. A rear flange 76a of a sleeve 76 is fixedly inserted into the front ring portion 75a. A sleeve 77 is fixedly inserted into the sleeve 76. A rear end portion of the insert tube 20 is inserted into the sleeve 77.

As shown in FIG. 4, the insert tube 20 is removably connected to the sleeve 77. A connecting sleeve 78 is fixedly inserted into the rear end portion of the insert tube 20. The connecting sleeve 78 is provided on a rear end thereof with a flange 78a extending radially outwardly. This flange 78a is arranged on a rear end face of the sleeve 77. Also formed on the rear end face of the sleeve 77 is a sleeve-like threaded portion 77a projecting backwardly therefrom. A cap 79 having an aperture 79a is threadedly engaged with the threaded portion 77a. A packing 25 is interposed between the cap 79 and the flange 78a of the connecting sleeve 78. By tightening the cap 79, the packing 25 and the flange 78a are firmly sandwiched and fixed between the rear end face of the sleeve 77 and the cap 79. As a consequence, the insert tube 20 is connected to the sleeve 77 and thus to the body 10.

The insert tube 20, the sleeves 71, 74, 76 and 77 of the connecting mechanism 70, and the ring 72 are coaxial with the extension portion 12 of the body 10.

As shown in FIG. 4, a rear end portion of an accordion-like guide tube 26 for Guiding the brush 60 is fixed to an inner periphery of the connecting sleeve 83. The Guide tube 26 is allowed to extend through the insert tube 20 and the angle tube 30, and a distal end of the guide tube 26 is fixed to the distal end of the angle tube 30.

Since the construction of the angle tube 30 is similar to that of a general endoscope, detailed illustration thereof is omitted. The construction of the angle tube 30 will be briefly described. The angle tube 30 includes a plurality of annular joints rotatably connected to each other and arranged in a row, a braid covering outer peripheries of the joints, and a resin tube covering an outer periphery of the braid. The angle tube 30 is provided at its distal end with a hard chip 31 (see FIG. 1). A foremost joint is fixed to this chip 31.

Figure 5:
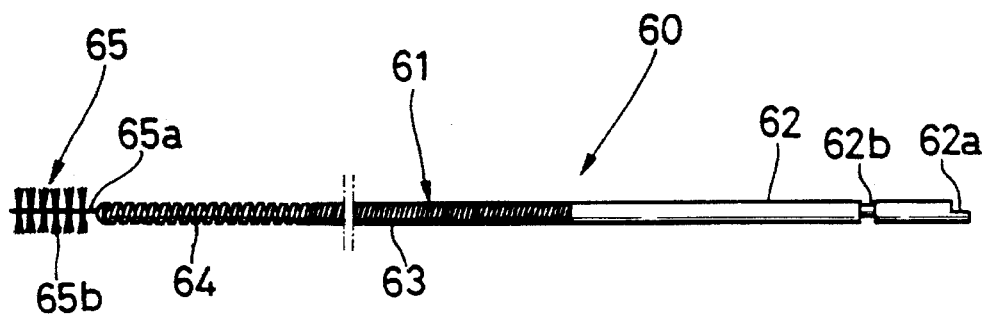
FIG. 5 is a side view showing a whole picture of the brush.

As shown in FIG. 5, the brush 60 includes an elongated rotation transmission portion 61 and a brush portion 65 coaxially extending from a distal end of the rotation transmission portion 61. The rotation transmission portion 61 includes a sectionally circular hard portion 62 formed of a metal rod, a first flexible portion 63 formed by spirally winding a metal wire, and a second flexible portion 64 likewise formed by spirally winding a metal wire, all arranged in this order from the basal end to the distal end. The first flexible portion 63 is densely wound so that adjacent turns are in contact with each other, while the second flexible portion 64 are roughly wound so that adjacent turns are spaced apart from each other. Owing to the foregoing arrangement, the second flexible portion 64 is more easily bent than the first flexible portion 63. A cut 62a is formed in a rear end of the hard portion 62, and an annular groove 62b is formed in an intermediate portion thereof. The brush portion 65 includes a core 65a formed by twisting a double-folded metal wire, and a number of hairs or bristles 65b formed, for example, of a resin are attached to the core 65a.

Next, a connecting mechanism 80 for connecting the motor 50 and the brush 60 will be described with reference to FIG. 4. This connecting mechanism 80 is coaxial with and opposite to the connecting mechanism 70 for the insert tube 20. A distal end of a connecting shaft 82 which is connected to an output shaft of the motor 50 and a rear end of a rotary sleeve 83 are inserted into the sleeve 71 and connected to each other. A connecting bit 84 is received in the rotary sleeve 83 and fixed by screws 85a and 85b. A cut 84a is formed in a distal end of the connecting bit 84. A collet mechanism 86 is attached to a distal end portion of the rotary sleeve 83. This collet mechanism 86 includes a sleeve 87 threadedly engaged with the distal end portion of the rotary sleeve 83, and a plurality of collet pieces 88 received between the sleeve 87 and the rotary sleeve 83. A rear end of the hard portion 62 (FIG. 5) of the brush 60 having the cut 62a is inserted into the distal end portion of the rotary sleeve 83 such that the rear end of the hard portion 62 of the brush 60 is brought into engagement with the distal end of the connecting bit 84 having the cut 84a, thereby rotation of the motor 50 is transmitted to the brush 60 through the connecting shaft 82, the rotary sleeve 83 and the connecting bit 84. By tightening the sleeve 87 of the collet mechanism 86 to the rotary sleeve 83 with the hard portion 62 of the brush 60 received in the rotary sleeve 83, a projection 88a projecting radially inwardly from a distal end of each collet piece 88 is caused to enter the annular groove 62b of the hard portion 62 owing to the function of the taper of the distal inner periphery of the sleeve 87 and the taper of the distal outer surface of each collet piece 88. By this, the brush 60 is prevented from escaping. Also, by reversely rotating the sleeve 87 of the collet mechanism 86, the brush 60 can be detached from the collet mechanism 86.

As mentioned, the rear end of the hard portion 62 of the brush 60 is connected to the motor 50 through the connecting mechanism 80, and the distal end portion of the hard portion 65 is inserted into the packing 25. The first flexible portion 63 is received in the guide tube 26 within the insert tube 20.

A border between the hard portion 62 and the first flexible portion 63 is generally coincident with the flange 78a of the connecting sleeve 78. The second flexible portion 64 is received in the guide tube 26 at the angle tube 30. The distal end of the second flexible portion 64 is generally coincident with the distal end of the angle tube 30. Therefore, the brush portion 65 projects from the distal end of the angle tube 30.

A battery (not shown) connected to the motor 50 is received in the grip portion 11 of the body 10. The grip portion 11 is provided with a switch control portion 15 for controlling the motor 50. By pulling the switch control portion 15 toward the grip portion 11 using an index finger of a doctor who holds the grip portion 11, the doctor can actuate the motor 50 to cause rotation of the brush 60.

Figure 2:
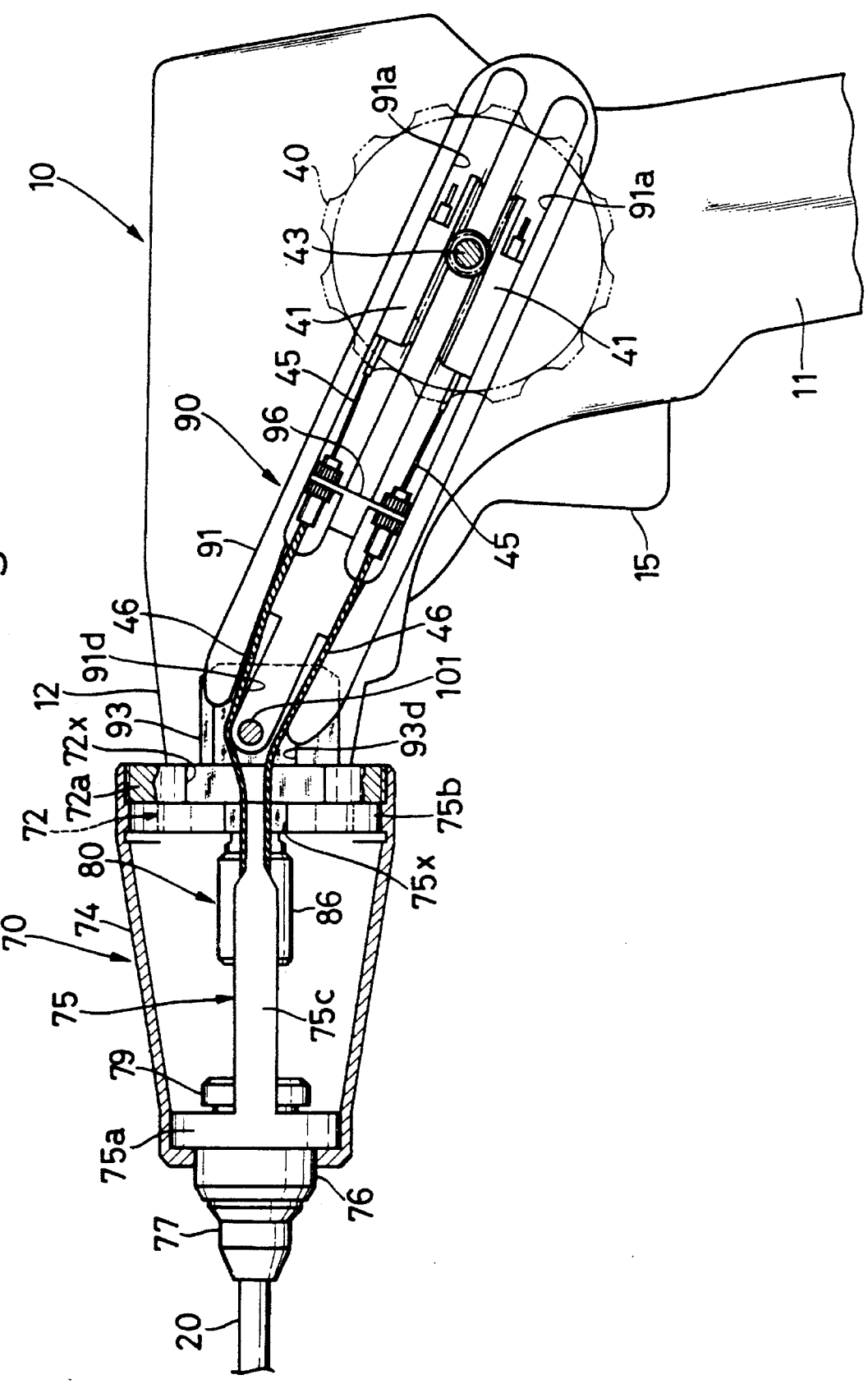
FIG. 2 is a side view, partly cutaway, showing an important portion of the medical instrument on an enlarged scale.

Next, a construction for remote controlling the angle tube 30 will be described in detail. As shown in FIGS. 1 to 3, the control dial 40 is mounted on the body 10 through an arm 90. As best shown in FIG. 3, the arm 90 includes an arm base 91 formed of an elongated plate, and an arm cover 92 fixedly superimposed on the arm base 91. A distal end of the arm base 91 is connected to the body 10 through a bracket 93. More specifically, a recess 72x is formed in a part of an outer periphery of the flange 72a, and a distal end of the bracket 93 is fixedly received in the recess 72x. The distal end of the arm base 91 is rotatably connected to a rear end of the bracket 93 such that rotational position of the arm base 91 is adjustable as later described in detail.

As shown in FIGS. 2 and 3, a pair of guide grooves 91a are formed in the arm base 91 in such a manner as to extend in a longitudinal direction of the arm base 91. A pair of racks 41 are slidably received in the guide grooves 91a. On the other hand, the control dial 40 is rotatably mounted on a rear end portion of the arm cover 92. A pinion 43 is mounted on the control dial 40 through a shaft 42. This pinion 43 is meshed with the pair of racks 41.

The pair of racks 41 and the distal end of the angle tube 30 are connected together through a pair of control wires 45. The control wires 45 are allowed to pierce respectively into a pair of flexible guide tubes 46 which are formed by spirally winding a metal wire. First, the guide tube 46 will be described in detail. Distal ends of the pair of guide tubes 46 are fixedly held in diametically or vertically opposite relation (FIG. 1) at the border between the insert tube 20 and the angle tube 30. As shown in FIG. 4, the guide tubes 46 are allowed to extend backwardly passing between the insert tube 20 and the guide tube 26, then through a pair of holes 20a formed in a rear end peripheral wall of the insert tube 20, and then through a pair of slant holes 77b formed in the sleeve 77 and a pair of cuts 76b formed in the sleeve 76.

As shown in FIGS. 2 and 3, the pair of guide tubes 46 are allowed to extend backwardly along an inner surface of one of the pair of connecting portions 75c of the support 75. A presser plate 95 extending along the connecting portion 75c is fixed to an inner surface of the connecting portion 75c. A central portion in a width direction of the presser plate 95 is fixed to the connecting portion 75c. The pair of guide tubes 46 are sandwiched between opposite side portions in the width direction of the presser plate 95 and the connecting portion 75c.

As shown in FIG. 2, the guide tubes 46 are allowed to extend further backwardly passing through a recess 75x formed in an outer periphery of the ring portion 75b of the support 75, then through the recess 72x of the ring 72 and a recess 93d of the bracket 93, and then through a recess 91d formed in a distal end portion of the arm base 91. Rear ends of the guide tubes 46 are fixed to an intermediate portion of the arm base 91 through a bracket 96.

The pair of control wires 45 are allowed to extend respectively through the pair of guide tubes 46, with distal ends of the control wires 45 allowed to project from the distal ends of the guide tubes 46 in such a manner as to be in diametically or vertically opposite relation (FIG. 1) to each other and fixed to the chip 31 on the distal end of the angle tube 30. Rear ends of the pair of control wires 45 are allowed to project respectively from the rear ends of the guide tubes 46 and fixed respectively to distal ends of the pair of racks 41.

Figure 6:
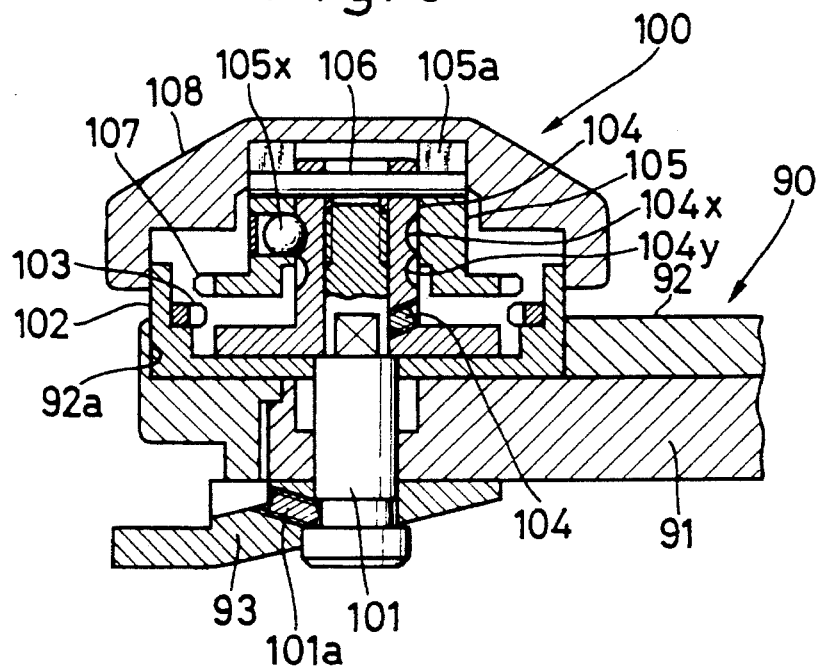
FIG. 6 is an enlarged sectional view showing a connecting mechanism for connecting an arm for retaining a control dial to the body.

Next, a connecting mechanism 100 for rotatably connecting the arm 90 to the body 10 will be described in detail. As shown in FIG. 6, a support shaft 101 is allowed to extend through the bracket 93 and the arm base 91 and fixed to the bracket 93 by a screw 101a. A hole 92a is formed in a distal end portion of the arm cover 92. A support sleeve 102 is received in this hole 92a and fixed to the arm base 91. A ring-like gear 103 is fixed to an inner periphery of the support sleeve 102. A guide sleeve 104 is threadedly engaged with an upper end outer periphery (FIG. 6) of the support shaft 101 and fixed to the support shaft 101 by a screw 104a. A retaining sleeve 105 is axially slidably mounted on an outer periphery of the guide sleeve 104. This retaining sleeve 105 is caused to be incapable of rotation relative to the guide sleeve 104 by a pin 106. This pin 106 is allowed to extend radially through an upper end portion of the guide sleeve 104. Opposite end portions of the pin 106 are received respectively in a pair of slits 105a formed in an upper end portion of the retaining sleeve 105. A gear 107 engageable with the gear 103 is formed on a lower end of the retaining sleeve 105.

The retaining sleeve 105 is capable of movement between a first position (hereinafter referred to the "engaged position") where the gears 103 and 107 are engaged with each other and a second position (hereinafter referred to the "non-engaged position") where the gears 103 and 107 are incapable of engagement. More specifically, two annular grooves 104x and 104y are formed in the outer periphery of the guide sleeve 104, and a ball 105x is mounted on the retaining sleeve 105. The ball 105x is biased radially inwardly by a spring not shown. A part of the ball 105x is allowed to project from an inner periphery of the retaining sleeve 105. By fitting the ball 105x into selected one of the annular grooves 104x and 104y, the guide sleeve 104 is held in the engaged position or the non-engaged position. A cap 108 is fixed to the upper end of the retaining sleeve 105.

With the above-mentioned construction, the doctor can adjust the rotational position of the arm 90 and thus the position of the control dial 40 by his thumb so that the control dial 40 can easily be manipulated by the thumb of his hand holding the grip portion 11 of the body 10. That is, as shown in FIG. 6, by pulling the retaining sleeve 105 with his hand holding the cap 108 of the connecting mechanism 100, the ball 105x is caused to fit into selected one of the annular grooves, 104x. In that condition, since the gears 103 and 107 are not in engagement with each other, the arm 90 is capable of rotation relative to the body 10. By pushing the cap 108 after rotating the arm 90 to a desired rotational position, the retaining sleeve 105 is caused to move toward the bracket 93 to fit the ball 105x into the remaining annular groove 104y so that the gears 103 and 107 are engaged with each other. As a result, the arm 90 is prohibited from rotation and thus the axis of the control dial 40 is held in a desired position.

Figure 7:
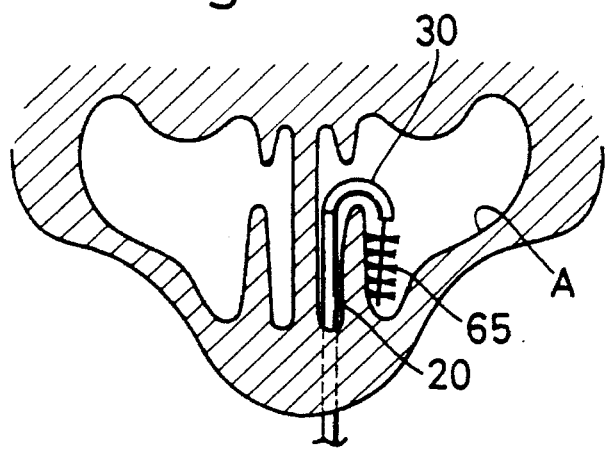
FIG. 7 is a plan view showing a using state of the medical instrument.

Holding the grip portion 11 of the body 10, the doctor inserts, as shown in FIG. 7, the angle tube 30 and the insert tube 20 from a patient's naris and advances them toward the maxillary sinus. At that time, the doctor manipulates the control dial 40 with his thumb to pull one of the wires 45 and loosen the other wire 45 through the pinion 43, so that the angle tube 30 is bent. By doing this, the brush portion 65 protecting from the distal end of the angle tube 30 can be brought into a deep portion of the maxillary sinus A.

In the state where the angle tube 30 is bent and the brush portion 65 is located in the deep portion of the maxillary sinus A, the doctor pushes the switch control portion 15 with his index finger to rotate the motor 50, so that the brush portion 63 is rotated. As a result, the mucous membrane peeled off over the entire inner periphery in the deep portion of the maxillary sinus A can be removed. The second flexible portion 64 of the brush portion 60 is received in the angle tube 30, and this second flexible portion 64 is bent in accordance with the bent shape of the angle tube 30. The second flexible portion 64 can rotate in such bent state. As a result, rotation of the motor 50 can be transmitted to the brush portion 65.

In treatment of sinusitis, a bodily liquid sometimes enters from an opening of the chip 31 of the angle tube 30 and flows along the guide tube 26 (FIG. 4). This bodily liquid is prevented from leaking outside by the packing 25 intimately attached to the outer periphery of the hard portion 62 of the brush 60.

After the completion of treatment, the sleeve 74 is removed. Then, the brush 60 is disconnected by rotating the sleeve 87 of the collet mechanism 86 and withdrawn from the collet mechanism 86 in order to be washed. Also, a wash water is supplied to the guide tube 26 to clean an inner peripheral surface thereof.

Figure 8:
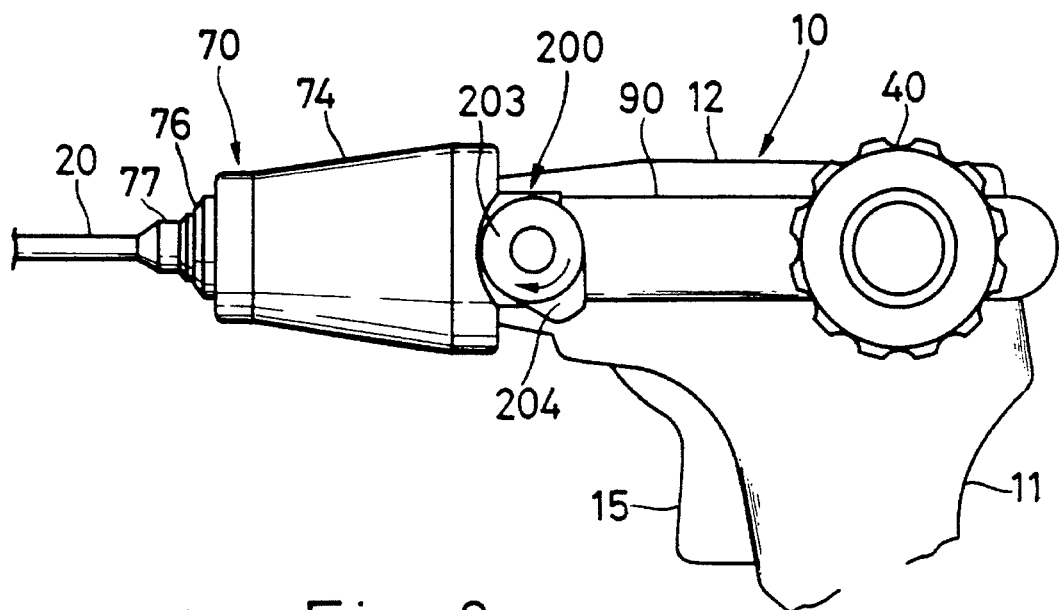
FIG. 8 is a side view of an important portion of a medical instrument for treating sinusitis according to another embodiment of the present invention.
Figure 9:
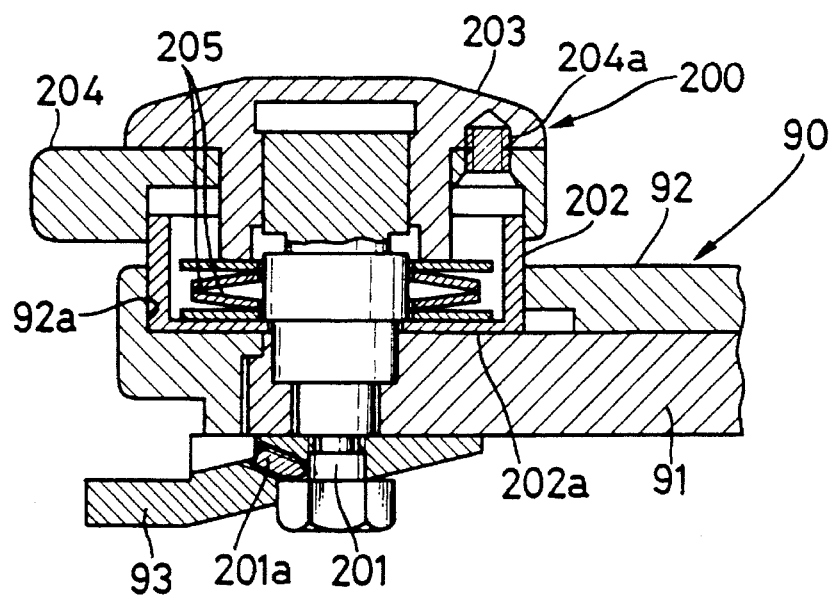
FIG. 9 is an enlarged sectional view of a connecting mechanism for connecting the arm to the body, which is employed in the medical instrument of FIG. 8.

Referring next to FIGS. 8 and 9, a modified embodiment of a connecting mechanism for connecting the arm to the body will be described. In this embodiment, like component parts as those of the preceding embodiment are denoted by like reference numerals and description thereof is omitted. In this connecting mechanism 200, a support shaft 201 is allowed to extend through the bracket 93 and the arm base 91 and fixed to the bracket 93 by a screw 201a. A support sleeve 202 is received in the hole 92a formed in the distal end portion of the arm cover 92 and fixed to the arm base 91. A cap 203 is threadedly engaged with an upper end outer periphery (FIG. 9) of the support shaft 201. A handle 204 is fixed to a lower surface of the cap 203 by a screw 204a. A pair of annular plate springs 205 are received in the support sleeve 202 between an upper surface of a flange 202a of the support sleeve 202 and the lower surface of the cap 203. As shown in FIG. 9, in the state where the cap 203 is loosely threadedly engaged with the support shaft 201, the support sleeve 202 is capable of rotation relative to the cap 203. As a result, the arm 90 is capable of rotation relative to the bracket 93. Moreover, since a frictional force is generated between a lower end of the cap 203 and the flange 202a of the support sleeve 202 owing to resilient force of the plate springs 205, the arm 90 can be lightly held in any rotational position. By rotating the cap 203 with the doctor's hand holding the handle 204 after the completion of rotational adjustment of the arm 90, the pair of plate springs 205 are brought into contact with each other over the entire surfaces thereof and the support sleeve 202 becomes unable to move relative to the cap 203. As a result, the arm 90 becomes unable to rotate relative to the bracket 93.

Figure 10:
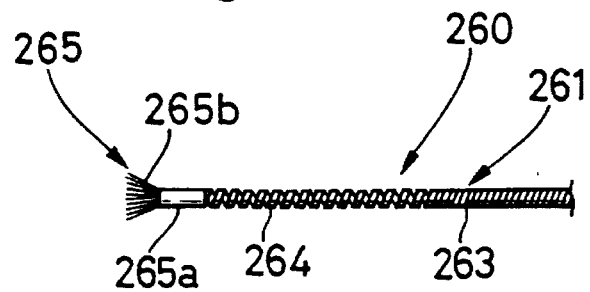
FIG. 10 is a side view of an important portion showing a modified example of the brush.

FIG. 10 shows a modified example of a brush 260. A rotation transmission portion 261 of this brush 260 is the same in construction to the afore-mentioned brush. The rotation transmission portion 261 includes a hard portion (not shown) and first and second flexible portions 263 and 264. A brush portion 265 comprises a short sleeve 265a and a number of hairs or bristles 263a attached to a distal end of the short sleeve 265a and diverging forwardly.

The present invention is not limited to the above embodiments, and many changes and modifications can be made. For example, the insert tube may be flexible. Alternatively, a rear portion of the insert tube may be hard and a front portion thereof may be flexible.

What is claimed is:

1. A medical instrument for treating sinusitis, comprising:
   (a) a body;
   (b) an insert tube extending from said body;
   (c) an angle tube extending from a distal end of said insert tube;
   (d) a remote control member mounted on said body and adapted to remotely control said angle tube through a control wire extending through said insert tube and said angle tube;
   (e) a motor mounted on said body; and
   (f) a brush having an elongated rotation transmission portion whose rear end is connected to said motor, and a brush portion attached to a distal end of said rotation transmission portion, said rotation transmission portion being allowed to extend through said insert tube and said angle tube, at least that portion of said rotation transmission portion corresponding to said angle tube being bendable, said brush portion being allowed to project outside from a distal end of said angle tube; and
   said angle tube being remotely controlled by said remote control member to be bent so that an angle between said brush portion and said insert tube is adjusted.

2. A medical instrument according to claim 1, in which said rotation transmission portion is provided on a basal end side thereof with a hard portion formed of a rod, said hard portion being connected to said motor.

3. A medical instrument according to claim 2, further comprising connecting mechanism for removably connecting said hard portion of said brush to a rotating shaft of said motor.

4. A medical instrument according to claim 1, in which said body is provided with a switch control portion for starting rotation of said motor.

5. A medical instrument according to claim 1, further comprising an arm whose distal end portion is rotatably mounted on said body through a connecting mechanism such that rotational position of said arm is adjustable, said remote control member being rotatably mounted on a rear end portion of said arm, said control wire being allowed to extend backwardly along said arm, a rear end portion of said control wire being in association with said remote control member.

6. A medical instrument according to claim 1, in which said body includes a grip portion and an extension portion extending from one end of said grip portion in a direction intersecting said grip portion, thereby forming a gun-like configuration as a whole, said body being provided with a trigger portion, said trigger portion being provided as a switch control portion for starting rotation of said motor, a distal end portion of an arm being rotatably mounted on a side surface of said extension portion of said body through a connecting mechanism such that rotational position of said arm is adjustable, said remote control member being rotatably mounted on a rear end portion of said arm, said control wire being allowed to extend backwardly along said arm, a rear end portion of said control wire being in association with said remote control member.

* * * * *